(12) United States Patent
Kugler

(10) Patent No.: US 12,398,233 B2
(45) Date of Patent: Aug. 26, 2025

(54) METHOD FOR PRODUCING A MIXTURE COMPRISING AT LEAST ONE COMPOUND HAVING AT LEAST TWO HYDROXY AND/OR AMINO GROUPS AND USE THEREOF FOR PRODUCING A POLYMER

(71) Applicant: RAMPF Advanced Polymers GmbH & Co. KG., Grafenberg (DE)

(72) Inventor: Michael Kugler, Pirmasens (DE)

(73) Assignee: RAMPF Advanced Polymers GmbH & Co. KG, Grafenberg (DE)

( * ) Notice: Subject to any disclaimer, the term of this patent is extended or adjusted under 35 U.S.C. 154(b) by 1008 days.

(21) Appl. No.: 17/416,758

(22) PCT Filed: Dec. 20, 2019

(86) PCT No.: PCT/EP2019/086553
§ 371 (c)(1),
(2) Date: Dec. 3, 2021

(87) PCT Pub. No.: WO2020/127890
PCT Pub. Date: Jun. 25, 2020

(65) Prior Publication Data
US 2022/0153914 A1 May 19, 2022

(30) Foreign Application Priority Data
Dec. 21, 2018 (DE) .................. 10 2018 222 887.6

(51) Int. Cl.
| | | |
|---|---|---|
| C08G 18/42 | (2006.01) | |
| C08G 63/52 | (2006.01) | |
| C08G 63/81 | (2006.01) | |
| C08G 63/85 | (2006.01) | |
| C08J 9/12 | (2006.01) | |

(52) U.S. Cl.
CPC ......... *C08G 18/4288* (2013.01); *C08G 63/52* (2013.01); *C08G 63/81* (2013.01); *C08G 63/85* (2013.01); *C08J 9/125* (2013.01); *C08G 2110/0025* (2021.01); *C08J 2203/10* (2013.01); *C08J 2205/10* (2013.01); *C08J 2375/06* (2013.01)

(58) Field of Classification Search
CPC .............. A61K 31/155; A61K 31/415; A61K 31/4164; A61K 31/4245; A61K 31/4453; A61K 31/4985; A61K 31/505; A61K 31/506; A61K 31/551; A61P 3/00; A61P 3/04; A61P 3/10; A61P 43/00; C07D 231/12; C07D 233/64; C07D 237/04; C07D 239/26; C07D 243/08; C07D 271/06; C07D 401/04; C07D 401/12; C07D 403/04; C07D 403/10; C07D 403/12; C07D 403/14; C07D 405/12; C07D 409/12; C07D 409/14; C07D 413/04; C07D 413/10; C07D 413/12; C07D 413/14; C07D 417/04; C07D 417/12; C07D 471/04; C07D 495/04
See application file for complete search history.

(56) References Cited

U.S. PATENT DOCUMENTS 11,118,308 B2 * 9/2021 Hallett .................. C12P 19/14

FOREIGN PATENT DOCUMENTS

| CN | 104557836 A | 4/2015 |
|---|---|---|
| EP | 2371805 A1 | 10/2006 |
| JP | 2002037867 A | 2/2002 |

OTHER PUBLICATIONS

Translation of JP 2002-037867 (Year: 2002).*
International Search Report and Written Opinion in PCT/EP2019/086553. Mailed Mar. 25, 2020. 37 pages.

* cited by examiner

*Primary Examiner* — John M Cooney
(74) *Attorney, Agent, or Firm* — Meunier Carlin & Curfman LLC

(57) ABSTRACT

The present invention relates to a method for producing a mixture comprising at least one compound having at least two hydroxy and/or amino groups made of a biomass material. The invention also relates to such a mixture and to the use thereof for producing a polymer such as for example a polyurethane foam.

18 Claims, No Drawings

METHOD FOR PRODUCING A MIXTURE COMPRISING AT LEAST ONE COMPOUND HAVING AT LEAST TWO HYDROXY AND/OR AMINO GROUPS AND USE THEREOF FOR PRODUCING A POLYMER

The present invention relates to a method for producing a mixture comprising at least one compound having at least two hydroxy and/or amino groups, to such a mixture and to the use thereof for producing a polymer.

Natural and, in particular, renewable sources of raw materials are becoming more and more important these days. Due to aspects of the sustainable use of finite resources and the fact that fossil raw materials are not available in unlimited quantities, renewable raw materials are becoming increasingly relevant.

The production of plastics requires large amounts of monomers, which often come from fossil sources. For many years, it has therefore been a goal of plastics production to be decoupled from finite raw material sources and to become oriented towards sustainable, renewable raw materials.

For the production of plastics, monomers are required that carry functional groups in order to convert them into polymers, i.e., long-chain molecules, in polymerisation. For example, polyaddition reactions, such as the production of polyurethanes, or polycondensation reactions, such as the production of polyesters or polyamides, require monomers having at least two functional groups that are reacted with one another.

For example, fatty acids having more than one functional group and ester polyols based on fatty acids having more than one functional group that come from natural, i.e., renewable raw material sources, are successfully used in the production of polyols and polyurethane plastics. An example of the use of such a fatty acid from renewable sources is the use of ricinoleic acid as a monomer for the production of ester polyols or in the form of glyceride (castor oil) as a polyol component in polyurethane production on an industrial scale. Because of its two functional groups, namely the hydroxy group and the carboxy group, ricinoleic acid is particularly suitable as a monomer for polyol and/or polyurethane production.

Monofunctional fatty acids such as oleic acid are also used as additives, among other things in the production of aromatic ester polyols, in order to lower the viscosity and introduce hydrophobic groups. The disadvantage of such monofunctional fatty acids is that they lead to chain termination during polymer production and can therefore only be added in smaller concentrations.

An increase in the functionality of unsaturated fatty acids can be achieved by means of epoxidation. Subsequent ring opening, i.e., hydroxylation, allows corresponding highly functional polyols or polyamines to be produced by means of reaction with water, alcohols and/or amines, which polyols or polyamines are also used extensively for the production of polyurethane plastics.

There is a wide variety of natural, renewable sources that contain multifunctional fatty acids, such as bark. Bark within the meaning of the present invention includes in particular the secondary dermal tissue (periderm) and the tertiary dermal tissue (outer bark) of trees, more preferably cork and outer bark. Sources that are available in large quantities and that are at best obtained as a by-product and can thus be put to a new use, such as birch bark, are of particular interest here. Birch bark, for example, is obtained in large quantities as a by-product of cellulose production and is currently used for energy, i.e., it is burned.

Bark contains large amounts of the natural biopolymer suberin, which is found in many of the cell walls of plants. Significant amounts of suberin, which are typically between 30 and 60 wt. %, are found in a wide variety of plant species, such as potatoes and cotton. In particular, however, large amounts of suberin are found in the cuticle of cork oak, Douglas fir, beech and birch. Cutin is also found, which is another natural biopolymer and also occurs in plants.

The fatty acids contained therein can be isolated from the bark by means of extraction. The fatty acids extracted from the bark are a mixture comprising carboxylic acids that comprise at least one further functional group, for example a hydroxy, epoxy and/or acid group.

DE 829 447 C describes the use of extraction to obtain higher molecular weight organic acids from bark.

U.S. Pat. No. 6,768,016 B2 describes a method for obtaining fatty acids from birch bark and isolating the individual fatty acids.

EP 2 371 805 A1 describes the production of oligoesters and polyesters from suberin or cutin carboxylic acid mixtures that are obtained by means of hydrolysis. The suberin-fatty acid mixtures that are not further separated are esterified with carboxylic acids. The end products are mixtures of oligo-carboxylic acids.

Polyols and polyamines, for example, are required for polymerisation reactions such as the production of polyurethanes, polyesters, polyamides and others. If corresponding substances from natural sources are used, they often have to be extracted in a laborious manner and, in particular, purified in order to be suitable for polymerisation reactions. Some methods also include the use of toxic substances such as dimethyl sulfate, the use of which should be minimised for reasons of occupational safety and environmental protection and also results in increased process costs.

The aspects mentioned above are disadvantages of the known methods from the prior art. It is therefore the object of the present invention to overcome the disadvantages known from the prior art. The present invention is directed to a production method, as well as to mixtures of compounds and to the use of corresponding mixtures in the production of polymers that overcome the disadvantages mentioned above.

It has surprisingly been found that not only pure fatty acids but also the mixtures according to the invention can be used for the production of polymers. From the mixtures, for example, plastics such as polyurethanes, polyesters or polyamides having excellent product properties can be produced, which plastics can compete with or even exceed plastics made from commercially available, pure monomers, in particular with regard to their mechanical properties, such as compressive and flexural strength. In addition, the significant simplification of the method by avoiding additional cleaning and isolation steps, as are usually used in the prior art, increases the economic viability of the method and the mixtures and polymers derived therefrom by saving time, minimising technical costs and reducing production costs.

Furthermore, the use of the mixtures according to the invention produced from biomass material supports the conservation of raw material resources and increases the proportion of renewable raw materials in the plastics sector. Likewise, by refining its components, a waste product becomes a valuable raw material for further value creation. The choice of an easily accessible and inexpensive starting material also increases the economic viability of the method according to the invention.

Another advantage of using natural raw material sources is that the substance mixtures obtained comprise a large number of functional groups that can be functionalised orthogonally and that allow further tailor-made functionalisations for special applications.

DESCRIPTION OF THE INVENTION

The invention relates to a method for producing a mixture comprising at least one compound (I) having at least two hydroxy and/or amino groups, the method comprising the following steps:
- a) providing at least one biomass material, preferably peels and/or bark,
- b) treating the at least one biomass material from step a) with at least one first organic solvent at an elevated temperature,
- c) separating the solid from the mixture obtained after step b),
- d) treating the solid obtained after step c) with at least one second solvent under alkaline conditions at an elevated temperature,
- e) separating the liquid phase from the mixture obtained after step d),
- f) at least partially removing the at least one second solvent from the liquid phase obtained after step e),
- g) reacting the mixture obtained after step f) with at least one compound (II) having at least two hydroxy and/or amino groups.

In step a), at least one biomass material, i.e., a biomass material or a mixture of two or more biomass materials, is provided. The biomass material can comprise biological material, for example plants or material derived from plants, such as secondary products, by-products, residues or waste. The biomass material can be present as fresh biomass, i.e., biomass including at least part of the naturally contained water, as dry biomass, or as a mixture thereof. The biomass material may come from trees and/or bushes. Biomass material from trees can come from birches, beeches, oaks, preferably cork oaks, pines, firs, preferably Douglas firs, and/or spruces, for example. Biomass material from bushes can come from yews, lilacs and/or brooms, for example. The biomass material can come from subterranean or aboveground plant organs and include, for example, roots, fruit peels, seeds, seed hairs, such as cotton, and/or bark. Fruit peels include, for example, potato peels and maize husks. In one embodiment, the biomass material comprises bark, in particular the secondary and/or tertiary dermal tissue of trees, more preferably cork and/or outer bark, in particular of birch trees.

The biomass material can be provided in an untreated or comminuted form. In one embodiment, the biomass material is provided in a comminuted form, for example as cuttings, shredded material, pellets, shavings, chips, granules, fibres, ground material, powder, or a mixture thereof. Comminuted biomass material typically has a particle size of about 0.1 to 10 cm, preferably up to 5 cm, more preferably up to 2 cm and even more preferably up to 1 cm.

In one embodiment, the at least one biomass material is treated with a first organic solvent in step b). In one embodiment, the at least one biomass material is treated with more than one first organic solvent in step b), i.e., with a solvent mixture, such as a mixture of two, three or four solvents. The at least one first organic solvent preferably comprises acetone, dichloromethane, benzene, or a mixture thereof. The at least one first organic solvent preferably comprises acetone.

Step b) is carried out at an elevated temperature, i.e., at a temperature greater than room temperature, i.e., >20° C. Step b) is preferably carried out at 30-200° C., more preferably at 50-150° C., even more preferably at 60-120° C.

In one embodiment, step b) is carried out at normal pressure, i.e., at approximately 1 bar. In another embodiment, step b) is carried out at reduced pressure, i.e., at less than 1 bar. Step b) is preferably carried out at reduced pressure, for example at 150-800 mbar, preferably 150-500 mbar, more preferably 200-400 mbar.

Step b) is carried out, for example, for 1-300 hours, preferably 20-400 hours, even more preferably 60-300 hours and even more preferably 90-180 hours. The duration of method step b) can, for example, depend on the type, amount and particle size of the at least one biomass material; the type and amount of the at least one first organic solvent; and the type and amount of substance to be extracted. The substance to be extracted can, for example, be a non-polar, organic substance and optionally comprise betulin, betulinic acid, lupeol and/or derivatives thereof. The substance to be extracted is preferably dissolved in the first organic solvent.

Separating the solid in step c) can include, for example, filtration such as hot filtration, centrifugation and/or decantation. Step c) can furthermore also comprise washing the separated solid with at least one first solvent and subsequent filtration.

In one embodiment, the solid obtained after step c) is treated with a second solvent in step d). In one embodiment, the solid obtained after step c) is treated in step d) with more than one second solvent, i.e., with a solvent mixture. The solvent mixture comprises at least two, i.e., two, three, four or more solvents. The at least one second solvent preferably comprises at least one protic solvent. The at least one second solvent is preferably isopropanol, ethanol, water, or a mixture thereof. The at least one second solvent preferably comprises isopropanol.

Step d) is preferably carried out in the presence of at least one alkaline compound, such as, for example, in the presence of a hydroxide, a carbonate, a hydrogen carbonate, or mixtures thereof. More preferably, step d) is carried out in the presence of a hydroxide such as NaOH and/or KOH, in particular NaOH. The at least one alkaline compound is preferably dissolved in one of the at least one second solvent. The at least one alkaline compound is able to generate alkaline conditions, i.e., a pH>7.0, in step d). In one embodiment, the pH in step d) is >7.0-14.0 and preferably >8.0-14.0.

Step d) is carried out at an elevated temperature, i.e., at a temperature greater than room temperature, i.e., >20° C. Step d) is preferably carried out at 30-200° C., more preferably at 50-150° C., even more preferably at 60-120° C.

In one embodiment, step d) is carried out at normal pressure, i.e., at approximately 1 bar. In another embodiment, step d) is carried out at reduced pressure, i.e., at less than 1 bar.

The duration of method step d) can depend, for example, on the at least one biomass material, the particle size of the at least one biomass material, the at least one second solvent and the mass ratio of biomass material to solvent. Step d) is carried out, for example, for 1-1000 min, more preferably 20-500 min, even more preferably 60-300 min, in particular 90-180 min.

In step d), fatty acids and/or derivatives thereof are preferably extracted from the solid into the solvent phase. For the purposes of the invention, fatty acids and derivatives thereof are compounds that comprise at least one carboxyl group, preferably one or two carboxyl groups, and a branched or unbranched, saturated or unsaturated hydrocarbon functional group, preferably having 12-26 carbon atoms.

For the purposes of the invention, fatty acids and derivatives thereof can have at least one further functional group such as, for example, at least one hydroxy group, at least one epoxy group and/or at least one unsaturated C—C bond. In particular, in step d) fatty acids and derivatives thereof comprising saturated and/or unsaturated $C_{12}$-$C_{26}$ fatty acids and derivatives thereof, preferably saturated and/or unsaturated $C_{12}$-$C_{24}$ fatty acids and derivatives thereof, preferably saturated and/or unsaturated $C_{14}$-$C_{24}$ fatty acids and derivatives thereof and more preferably saturated and/or unsaturated $C_{14}$-$C_{22}$ fatty acids and derivatives thereof, are extracted. Fatty acids and derivatives thereof comprising octadec-9-enedioic acid, 18-hydroxyoctadec-9-enoic acid, 9,16-dihydroxyhexadecanoic acid, 9,10-epoxy-18-hydroxyoctadecanoic acid, 20-hydroxyeicosanoic acid, 9,10,18-trihydroxyoctadecanoic acid, docosanedioic acid, 22-hydroxydocosanoic acid, or mixtures thereof are preferably extracted.

Step d) is preferably carried out under conditions in which the further functional groups contained in the fatty acids and/or derivatives thereof remain unchanged, i.e., do not react. This is ensured in particular by the mild reaction conditions according to the invention. It is preferred that no strong acids or bases are used in the extraction step in order, for example, to prevent ring opening of any epoxides that may be present.

Separating the liquid phase in step e) can include, for example, filtration, centrifugation and/or decantation. Step e) preferably comprises hot filtration of the liquid phase. The temperature in the hot filtration is >20° C. and is preferably 30-200° C., more preferably 50-150° C. and even more preferably 60-120° C. The fatty acids to be extracted and/or derivatives thereof are preferably located in the at least one second solvent. Step e) can furthermore comprise washing the separated solid with at least one second solvent and subsequent filtration. In the latter case, the liquid phases are combined.

At least partially removing the at least one second solvent in step f) can include, for example, distillation, filtration, evaporation, centrifugation and/or vacuum drying. Step f) preferably comprises cooling the liquid phase obtained after step e), preferably to a temperature 20° C., in particular 0° C., and subsequent filtration. At least partially removing in step f) is understood to mean that at least 70 wt. % of the at least one second solvent relative to the total mass of the at least one second solvent is removed. Preferably, at least 80 wt. %, more preferably at least 90 wt. %, even more preferably at least 95 wt. %, and even more preferably at least 99 wt. % of the at least one second solvent relative to the total mass of the at least one second solvent is removed. In a preferred embodiment, the at least one second solvent is removed until a solid residue forms at room temperature, i.e., at 20° C.

If necessary, the mixture obtained in step f) can be subjected to at least one purification step, i.e., one, two, three or more purification steps, before the reaction in step g). A suitable purification step can include, for example, recrystallisation, resuspension in a polar solvent or solvent mixture, such as water and/or an alcohol, and subsequent at least partial removal of the polar solvent or solvent mixture, or other methods known to a person skilled in the art.

The mixture obtained in step f) comprising fatty acids and/or derivatives thereof can, as described above, also contain epoxy groups and/or unsaturated C—C bonds.

In step g), the mixture obtained after step f) is reacted with at least one compound (II) having at least two hydroxy and/or amino groups. Compound (II) can thus comprise at least two hydroxy groups, preferably 2-5 hydroxy groups, or at least two amino groups, preferably 2-5 amino groups, or at least one hydroxy and at least one amino group, preferably one hydroxy and one amino group.

Compound (II) is preferably selected from the group consisting of a polyol such as a diol, triol, tetraol or pentaol, an amino polyol such as an amino diol, amino triol, amino tetraol or amino pentaol, a polyamine such as a diamine, triamine, tetraamine or pentaamine, a polyamino alcohol such as a diamine monoalcohol, triamine monoalcohol, tetraamine monoalcohol or pentaamine monoalcohol, an amino alcohol, i.e., a monoamino monoalcohol, a polyamino polyol, or a mixture thereof.

Compound (II) is preferably selected from linear, cyclic or branched polyalkylene oxide, alkyl and alkenyl compounds having at least two hydroxy and/or amino groups, and mixtures thereof. Compound (II) is more preferably selected from linear, cyclic or branched poly($C_2$-$C_5$ alkylene oxide), $C_1$-$C_{30}$ alkyl and $C_2$-$C_{30}$ alkenyl compounds having at least two hydroxy and/or amino groups, and mixtures thereof. Compound (II) is even more preferably selected from linear, cyclic or branched poly($C_2$-$C_5$ alkylene oxide), $C_1$-$C_{10}$ alkyl and $C_2$-$C_{10}$ alkenyl compounds having at least two hydroxy and/or amino groups, and mixtures thereof. In particular, compound (II) is selected from a diol, triol, diamine, triamine, amino alcohol or a mixture thereof, preferably from diethylene glycol, dipropylene glycol, ethanolamine, ethylenediamine, propanediamine, butanediol, 1,2-butanediamine, 1,3-butanediamine or a mixture thereof, in particular diethylene glycol.

Reacting the mixture obtained after step f) with at least one compound (II) takes place in step g) at an elevated temperature, i.e., at >20° C. The temperature in step g) is preferably 50-400° C., more preferably 150-300° C., even more preferably 200-300° C.

In one embodiment, step g) is carried out at normal pressure, i.e., at approximately 1 bar. In another embodiment, step g) is carried out at reduced pressure, i.e., at less than 1 bar. Step g) is preferably carried out at reduced pressure, for example 150-800 mbar, preferably 150-500 mbar, more preferably 150-350 mbar.

Step g) is preferably carried out in the presence of a catalyst. In one embodiment, the reaction in step g) is carried out without a catalyst. In one embodiment, step g) comprises distillation and preferably azeotropic distillation. In a preferred embodiment, the reaction in step g) is carried out in the presence of a catalyst. Suitable catalysts are, for example, organometallic and/or basic catalysts. Examples of suitable catalysts include titanium tetrabutoxide, stannous octoate, manganese acetate, dibutyltin dilaurate, potassium acetate, potassium hydroxide or a combination thereof, preferably titanium tetrabutoxide.

The duration of step g) depends, for example, on the type and concentration of the at least one compound (II), the reaction temperature, the reaction pressure and, if appropriate, the type and concentration of the catalyst. Step g) is carried out, for example, for 30-2400 min, more preferably 120-1200 min, even more preferably 180-600 min.

The invention further relates to a method for producing a mixture comprising at least one compound (I) having at least two hydroxy and/or amino groups, the method comprising the following steps:

a) providing at least one biomass material, preferably peels and/or bark,
b) treating the at least one biomass material from step a) with at least one first organic solvent at an elevated temperature,
c) separating the solid from the mixture obtained after step b),
d) treating the solid obtained after step c) with at least one second solvent under alkaline conditions at an elevated temperature,
e) separating the liquid phase from the mixture obtained after step d),
f) at least partially removing the at least one second solvent from the liquid phase obtained after step e),
f1) at least partially reacting the mixture obtained after step f), containing epoxy groups and/or unsaturated C—C bonds, in an oxidation and/or addition reaction, and
g) reacting the mixture obtained after step f1) with at least one compound (II) having at least two hydroxy and/or amino groups.

The above specifications with regard to steps a), b), c), d), e), and f) are to be applied to the method according to the invention comprising the additional step f1).

At least partially reacting in step f1) can comprise an oxidation reaction and/or an addition reaction. In one embodiment, at least partially reacting in step f1) comprises an oxidation reaction and preferably ozonolysis or hydrogen peroxide-mediated oxidation. In one embodiment, at least partially reacting in step f1) comprises an addition reaction and preferably a nucleophilic addition or a cycloaddition, such as, for example, a Diels-Alder reaction. The addition reaction can comprise reaction with an unsaturated acid anhydride, preferably maleic anhydride, a mono- or polyamine, a mono- or polyol, or a mixture thereof.

At least partially reacting in step f1) means reacting at least 50% of the functional groups that are reactive for the conversion reaction of the mixture obtained after step f). Preferably, at least partially reacting means reacting 50-100%, preferably 60-100%, more preferably 70-100%, even more preferably 80-100% and even more preferably 90-100% of the functional groups of the mixture obtained after step f), which groups are reactive for the conversion reaction. Examples of reactive functional groups of the mixture obtained after step f) include epoxy groups, hydroxy groups, carboxy groups, unsaturated C—C bonds, for example C—C double bonds, and/or ester groups.

At least partially reacting in step f1) can optionally be carried out at an elevated temperature, i.e., at >20° C., for example at 20-200° C.

If necessary, step f1) is carried out in the presence of a catalyst. In one embodiment, the reaction in step f1) is carried out without a catalyst. In another embodiment, the reaction in step f1) is carried out in the presence of a catalyst. Suitable catalysts are, for example, organometallic and/or basic catalysts. Examples of suitable catalysts include titanium tetrabutoxide, stannous octoate, manganese acetate, dibutyltin dilaurate, potassium acetate, potassium hydroxide or a combination thereof, preferably titanium tetrabutoxide.

The above statements regarding step g) can be applied analogously to the reaction of the mixture obtained after step f1).

The reaction according to the invention in step g) and, where applicable, step f1) results in mixtures that are distinguished by increased functionality. Compared to compounds from the prior art, the number of hydroxy and/or amino groups in the mixture is increased. This is particularly advantageous with regard to the reactivity of the mixture, for example in a polymerisation reaction. It has surprisingly been found that polymers resulting from a polymerisation of the mixture have improved mechanical properties. In addition, the reaction according to the invention in step g) and, where applicable, step f1) results in a mixture having improved viscosity, which mixture is suitable for the production of polymers such as, for example, polyurethanes or polyesters, without further intermediate steps. Furthermore, the mixtures according to the invention have improved emulsifiability with hydrophobic blowing agents such as, for example, pentane, which has a particularly advantageous impact on the production of polymer foams.

The invention further relates to a mixture comprising at least one compound (I) having at least two hydroxy and/or amino groups, obtainable by a method described above. Compound (I) preferably comprises at least one compound A, B, C and/or D, each having at least two hydroxy and/or amino groups, compound A being

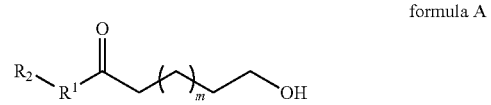

formula A where m=8-22, preferably 10-22, more preferably 12-22, even more preferably 12-20 and even more preferably 14-18,
compound B being

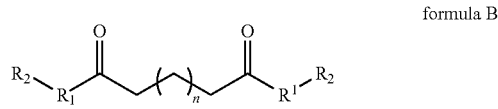

formula B where n=8-22, preferably 10-22, more preferably 12-22, even more preferably 12-20 and even more preferably 14-18,
compound C being

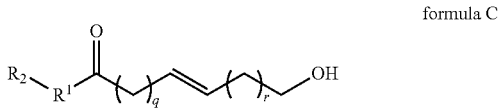

formula C where q=4-11 and r=4-11, preferably q=5-11 and r=5-11, more preferably q=6-11 and r=6-11, even more preferably q=6-10 and r=6-10 and even more preferably q=7-9 and r=7-9,
and compound D being

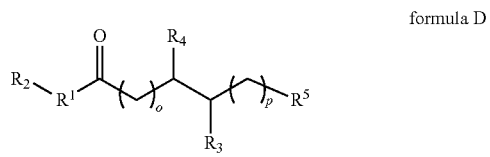

formula D where o=4-11 and p=4-11, preferably o=5-11 and p=5-11, more preferably o=6-11 and p=6-11, even more preferably o=6-10 and p=6-10 and even more preferably o=7-9 and p=7-9, where
$R^1$=O or NH;
$R^2$ is selected from the group consisting of a monoalcohol, polyol, monoamine, polyamine, polyamino alcohol, amino alcohol, amino polyol, polyamino polyol, or a mixture thereof;
$R^3$ is selected from OH, O—$R^2$ or NH—$R^2$;
$R^4$ is selected from OH, O—$R^2$ or NH—$R^2$;
With the proviso that $R^3$=OH when $R^4$=O—$R^2$ or NH—$R^2$ and with the proviso that $R^4$=OH when $R^3$=O—$R^2$ or NH—$R^2$; and
$R^5$ is selected from —COR$^1$R$^2$ and —CH$_2$OH.

$R^2$ is preferably selected from linear, cyclic or branched polyalkylene oxide, alkyl and alkenyl compounds having at least one hydroxy and/or amino group, and mixtures thereof. At least one hydroxy and/or amino group comprises at least one hydroxy group; at least one amino group; and at least one hydroxy group and at least one amino group.

More preferably, $R^2$ is selected from linear, cyclic or branched poly($C_2$-$C_5$ alkylene oxide), $C_1$-$C_{30}$ alkyl and $C_2$-$C_{30}$ alkenyl compounds having at least one hydroxy and/or amino group, and mixtures thereof. Even more preferably, $R^2$ is selected from linear, cyclic and branched poly($C_2$-$C_5$ alkylene oxide), $C_1$-$C_{10}$ alkyl and $C_2$-$C_{10}$ alkenyl compounds having at least one hydroxy and/or amino group, and mixtures thereof. In particular, $R^2$ is selected from a monoalcohol, a diol, a monoamine, a diamine and an amino alcohol of a linear, cyclic or branched poly($C_2$-$C_5$ alkylene oxide), $C_1$-$C_{10}$ alkyl or $C_2$-$C_{10}$ alkenyl compound, or a mixture thereof.

$R^2$ is particularly preferably selected from CH$_2$CH$_2$OCH$_2$CH$_3$, a dipropylene glycol functional group such as CH$_2$CH(CH$_3$)OCH(CH$_3$)CH$_2$OH, CH(CH$_3$)CH$_2$OCH$_2$CH(OH)CH$_3$, or CH$_2$CH(CH$_3$)OCH$_2$CH(OH)CH$_3$, CH$_2$CH$_2$OH, CH$_2$CH$_2$NH$_2$, a propanamine functional group such as CH$_2$CH$_2$CH$_2$NH$_2$ or CH$_2$CH(NH$_2$)CH$_3$, a butanol functional group such as CH$_2$CH$_2$CH$_2$CH$_2$OH, CH$_2$CH(OH)CH$_2$CH$_3$, or CH$_2$CH$_2$CH(OH)CH$_3$, a butanamine functional group such as CH$_2$CH$_2$CH$_2$CH$_2$NH$_2$, CH$_2$CH(NH$_2$)CH$_2$CH$_3$, or CH$_2$CH$_2$CH(NH$_2$)CH$_3$, or a mixture thereof, in particular CH$_2$CH$_2$OCH$_2$CH$_3$.

The mixture comprising at least one compound (I) having at least two hydroxy and/or amino groups preferably has a viscosity (determined by the method according to DIN 53019) of 1-250,000 mPas/50° C., preferably 1-100,000 mPas/50° C., more preferably 1-10,000 mPas/50° C. and even more preferably 5-10,000 mPas/50° C.

The mixture comprising at least one compound (I) having at least two hydroxy and/or amino groups optionally has a hydroxy number (determined by the method according to ASTM E 1899-08) of 1-1000 mg KOH/g, preferably 5-800 mg KOH/g, more preferably 50-700 mg KOH/g.

The proportion of compounds A, B, C and/or D in the total mixture is preferably at least 20 wt. %, more preferably at least 30 wt. %, even more preferably at least 40 wt. % and most preferably at least 50 wt. %.

During the reaction in step g), compounds from the mixture obtained after step f) or f1) can also react with one another. The mixture comprising at least one compound (I) having at least two hydroxy and/or amino groups can thus optionally comprise homo- and/or heterodimers, homo- and/or heterotrimers, homo- and/or hetero-oligomers and/or homo- and/or heteropolymers of compounds from the mixture obtained after step f) or f1). For the purposes of the invention, homodimers, homotrimers, homo-oligomers and homopolymers are molecules that are made up of identical building blocks. For the purposes of the invention, heterodimers, heterotrimers, hetero-oligomers and heteropolymers are molecules that are made up of different building blocks. The substances obtained in this way can also comprise at least two hydroxy and/or amino groups.

Preferably, the mixture comprising at least one compound (I) having at least two hydroxy and/or amino groups comprises homo- and/or heterodimers, homo- and/or heterotrimers, homo- and/or hetero-oligomers and/or homo- and/or heteropolymers, which result from the reaction of substances A, B, C and/or D with one another. More preferably, the mixture comprises at least one compound (I) having at least two hydroxy and/or amino groups of homo- and/or heterodimers, homo- and/or heterotrimers and/or homo- and/or hetero-oligomers, which result from the reaction of substances A, B, C and/or D with one another. Even more preferably, the mixture comprises at least one compound (I) having at least two hydroxy and/or amino groups of homo- and/or heterodimers and/or homo- and/or heterotrimers, which result from the reaction of substances A, B, C and/or D with one another.

One aspect of the invention relates to the use of the mixture comprising at least one compound (I) having at least two hydroxy and/or amino groups for the production of a polymer, the polymer optionally being a polyurethane, polyisocyanurate, polyurea, polyester, polyamide, polycarbonate, polyether, or a combination thereof. The mixture comprising at least one compound (I) having at least two hydroxy and/or amino groups is preferably used to produce a polyurethane. The polymer can be present, for example, as a solid, for example as a powder, foam, flake or film. The mixture comprising at least one compound (I) having at least two hydroxy and/or amino groups is preferably used to produce a polymer foam and more preferably a polyurethane foam.

One aspect of the invention further relates to a polyurethane comprising a mixture comprising at least one compound (I) having at least two hydroxy and/or amino groups as a polymer building block.

PRODUCTION EXAMPLES

Determining the Viscosity
The viscosity was determined in accordance with DIN 53019 using a DV-II viscometer having an LV 64 spindle (Brookfield).
Determining the Hydroxyl Number
The hydroxyl number was determined in accordance with ASTM E 1899-08 using a 907 Titrando measuring device (Metrohm).
Determining the Compressive Strength
The compressive strength was determined in accordance with DIN 53421 using a Z010 universal testing machine (Zwick Roell).
Determining the Flexural Strength
The flexural strength was determined in accordance with DIN EN ISO 178 using a Z010 universal testing machine (Zwick Roell).
Substances Used
Diethylene glycol was obtained from Brenntag GmbH (Essen, Germany).
The isocyanate having the trade name Desmodur 44V20 was obtained from Covestro.
Tetrabutyl titanate was obtained from Lehmann & Voss & Co. KG (Hamburg, Germany) under the trade name Tyzor TnBT.
The reference polyol used was obtained from Covestro under the trade name Baymer VP.PU 25HB55.

The stabiliser having the trade name DC 193 was obtained from Evonik (Germany). The stabiliser having the designation LV 33 was also obtained from Evonik (Germany).

The catalyst PC CAT NP10 (NP 10) was obtained from Nitroil Europe Handels GmbH (Germany).

Production of Polyester Polyol

Example 1

Birch bark was reacted according to a method known from the prior art, which comprises treating the birch bark in the presence of acetone for several hours at an elevated temperature and refluxing in the presence of isopropanol and NaOH, the fatty acids contained in the birch bark being transferred into the solvent. After removal of the solvent and purification and drying, a fatty acid mixture that was solid at room temperature was obtained. This fatty acid mixture was composed of different, multifunctional fatty acids, which included both free acid functions and ester functions and were present as salts.

Example 2

50 parts of the fatty acid mixture from Example 1 were transferred into a reaction vessel, and 50 parts of diethylene glycol were added. The mixture was heated to 200° C., and the water of reaction was distilled off. At 200° C., 0.1 parts of tetrabutyl titanate were added. The mixture was heated further to 230° C. and then the pressure was reduced to 200 mbar in order to complete the esterification reaction.

The brownish clear ester polyol obtained in this way had a viscosity of 190 mPas/50° C. and a hydroxyl number of 505 mg KOH/g.

Production of Rigid Polyurethane Foams

Example 3

The ester polyol obtained in Example 2 was formulated with additives. For this purpose, 95 parts of polyol, 1 part of stabiliser DC 193, 0.7 parts of stabiliser LV 33, 0.3 parts of NP 10 and 3 parts of water were mixed. The mixture obtained was then reacted with 170 parts of Desmodur 44V10 to form a rigid polyurethane foam.

The rigid foam obtained had a density of 95 kg/m$^3$.

Comparative Example 1

According to Example 3, the commercially available comparison polyol Baymer VP PU 25HB55 (95 parts as a mixture with 1 part DC 193, 0.7 parts LV 33, 0.3 parts NP 10 and 3 parts water) was reacted with 150 parts Desmodur 44V20 to form a rigid foam.

The rigid foam obtained had a density of 96 kg/m$^3$.

The results of the compressive strength and flexural strength tests are shown in Table 1.

TABLE 1

Results of the compressive strength and flexural strength testing.

| | Compressive strength (MPa) | Flexural strength (MPa) |
|---|---|---|
| Example 3 | 0.88 | 1.36 |
| Comparative example 1 | 1.01 | 1.17 |

The rigid foam according to the invention from Example 3 has a higher flexural strength than the rigid foam from Comparative example 1, which was produced using a commercially available polyol. The compressive strength of the rigid foam according to the invention is slightly reduced.

The good mechanical properties, in particular the increased flexural strength, are surprising because the polyol from Example 3 is a mixture of different ester polyols. It has been shown that the use of ester polyols according to the invention in high concentrations is possible with constant and in some cases improved properties.

The use of ester polyol mixtures from natural sources such as birch bark in rigid polyurethane foam production leads to products having advantageous properties. This opens up a new source of naturally occurring raw materials that are suitable for industrial use and at the same time conserve resources, and that also lead to a reduction in the production costs of PU foams.

The invention claimed is:

1. A method for producing a mixture comprising at least one compound (I) having at least two hydroxy and/or amino groups, the method comprising the following steps:
   a) providing at least one biomass material,
   b) treating the at least one biomass material with at least one first organic solvent at a temperature of 30-200° C. to obtain a first mixture comprising a solid,
   c) separating the solid from the first mixture to obtain a separated solid,
   d) treating the separated solid with at least one second solvent under alkaline conditions at a temperature of 30-200° C. to obtain a second mixture comprising a liquid phase,
   e) separating the liquid phase from the second mixture to obtain a separated liquid phase,
   f) at least partially removing the at least one second solvent from the separated liquid phase to obtain a third mixture,
   g) reacting the third mixture with at least one compound (II) having at least two hydroxy and/or amino groups.

2. The method according to claim 1, wherein the at least one biomass material in comprises at least one of peels or bark.

3. The method according to claim 1, wherein the first organic solvent is selected from acetone, dichloromethane, benzene or a mixture thereof.

4. The method according to claim 1, wherein the at least one biomass material is treated with the at least one first organic solvent at 150-800 mbar.

5. The method according to claim 1, wherein separating the solid from the first mixture comprises hot filtration, centrifugation or decantation.

6. The method according to claim 1, wherein the second solvent is selected from isopropanol, ethanol, water or a mixture thereof.

7. The method according to claim 1, wherein the separated solid is treated with the at least one second solvent in the presence of a hydroxide, a carbonate, a hydrogen carbonate or a mixture thereof.

8. The method according to claim 1, the second mixture obtained by treating the separated solid comprises extracted $C_{12}$-$C_{26}$ fatty acids and derivatives thereof.

9. The method according to claim 1, wherein the separation of the liquid phase from the second mixture comprises at least one of filtration, centrifugation or decantation.

10. The method according to claim 1, wherein the at least partial removal of the at least one second solvent in comprises at least one of distillation, filtration, evaporation or centrifugation.

11. The method according to claim 1, wherein the at least one compound (II) having at least two hydroxy and/or amino groups is selected from the group consisting of a polyol, amino polyol, polyamine, polyamino alcohol, amino alcohol, polyamino polyol or a mixture thereof.

12. The method according to claim 11, wherein the at least one compound (II) having at least two hydroxy and/or amino groups is selected from a diol, triol, diamine, triamine, amino alcohol or a mixture thereof.

13. The method according to claim 1, wherein the third mixture is reacted with the at least one compound (II) having at least two hydroxy and/or amino groups at 20-400° C.

14. The method according to claim 1, wherein the third mixture is reacted with the at least one compound (II) having at least two hydroxy and/or amino groups in the presence of a catalyst.

15. The method according to claim 1, wherein the third mixture comprises a compound having at least one of epoxy groups or unsaturated CC bonds, and prior to reacting the third mixture with at least one compound (II) having at least two hydroxy and/or amino groups, the third mixture is at least partially reacted in at least one of an oxidation or addition reaction.

16. The method according to claim 15, wherein the oxidation or addition reaction comprises ozonolysis or hydrogen peroxide-mediated oxidation.

17. The method according to claim 15, wherein the oxidation or addition reaction comprises a nucleophilic addition or a cycloaddition.

18. The method according to claim 17, wherein the nucleophilic addition reaction comprises reaction with an unsaturated acid anhydride, a mono- or polyamine, a mono- or polyol or a mixture thereof.

* * * * *